United States Patent [19]
Mitri

[11] Patent Number: 5,715,559
[45] Date of Patent: Feb. 10, 1998

[54] CLEANING TOOL

[76] Inventor: George Mitri, 3730 Arbor Rd., Lakewood, Calif. 90712

[21] Appl. No.: 694,946

[22] Filed: Aug. 9, 1996

[51] Int. Cl.⁶ .............................. A47L 13/10; A61F 13/38
[52] U.S. Cl. .............................. 15/118; 15/209.1; 15/225; 15/244.1; 604/1
[58] Field of Search .................... 15/208, 209.1, 15/210.1, 223–226, 244.1, 118; 604/1

[56] References Cited

U.S. PATENT DOCUMENTS

| 1,650,412 | 11/1927 | Adams | 15/210.1 X |
| 1,785,512 | 12/1930 | Buttenheim | 15/210.1 |
| 1,866,862 | 7/1932 | Prestwich et al. | 15/225 X |
| 2,637,061 | 5/1953 | Ozdobinski | 15/226 |
| 2,744,279 | 5/1956 | Heber | 15/244.1 X |
| 3,281,884 | 11/1966 | Feil | 15/244.1 |
| 3,724,018 | 4/1973 | Sills | 15/244.1 |
| 3,724,463 | 4/1973 | Vail | 604/1 |
| 4,820,259 | 4/1989 | Stevens | 604/1 X |
| 5,214,821 | 6/1993 | Burrow et al. | 604/1 X |
| 5,279,015 | 1/1994 | Meiring | 15/225 X |

FOREIGN PATENT DOCUMENTS

| 89271 | 9/1983 | European Pat. Off. | 604/1 |
| 372914 | 4/1907 | France | 604/1 |
| 165314 | 2/1934 | Switzerland | 604/1 |
| 231981 | 4/1925 | United Kingdom | 15/210.1 |
| 85-05296 | 12/1985 | WIPO | 15/210.1 |

Primary Examiner—Mark Spisich
Attorney, Agent, or Firm—Curtis L. Harrington

[57] ABSTRACT

A cleaning tool has a stick or rod supporting a length of rope twisted material wound in a spiral pattern. A first embodiment includes a rope twisted spiral of material applied directly to a stick. In a second embodiment, the rope twisted spiral is applied over a wound layer of material wound in the standard manner and at right angles to the axis of the stick. This embodiment is in effect a padded spiral with the rope twisted material being padded underneath and cushioned by the standard material winding. In a third embodiment, a tightly spaced length of rope-wound material is attached to a stick. In a fourth embodiment, the tightly spaced length of rope-wound material is spiral cut to provide custom shaping to the ridges of the spiral shape. In a fifth embodiment, an extruded length of material with a 30° angle is wrapped onto a rod. In a sixth embodiment, the cleaning surface and the rod are integrally formed. In a seventh embodiment, a length of cut sponge is applied to the rod. In an eighth embodiment, a conically shaped under layer of wound cotton supports an over layer of rope cotton having constant cross section. In a ninth embodiment, an integrated structure has an overall sharply tapered shape but with a constant angled spiral ridge outer surface.

20 Claims, 3 Drawing Sheets

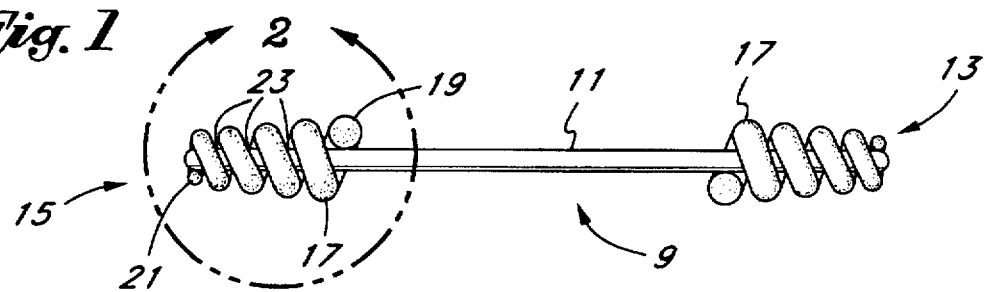
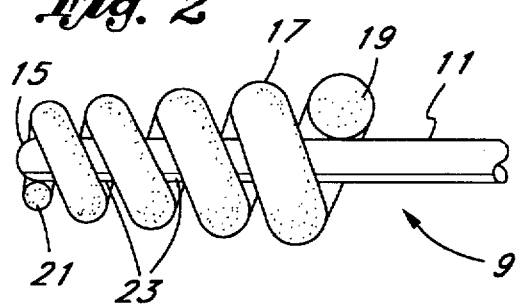
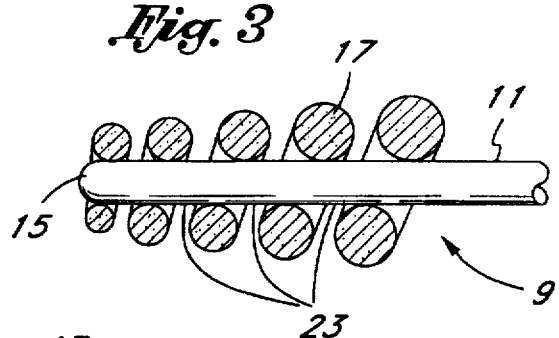
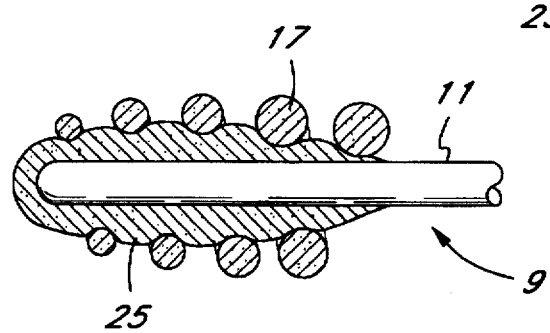
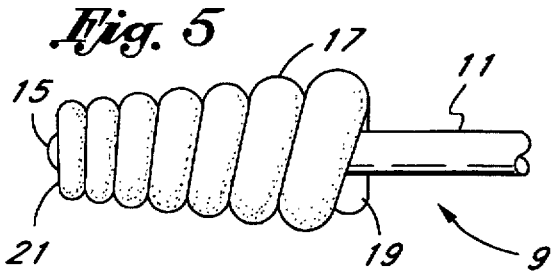
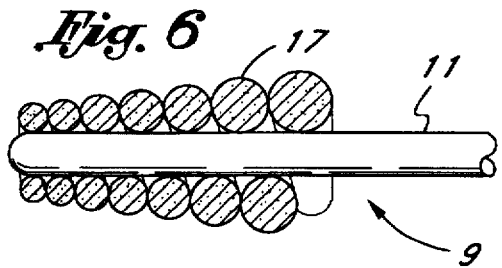
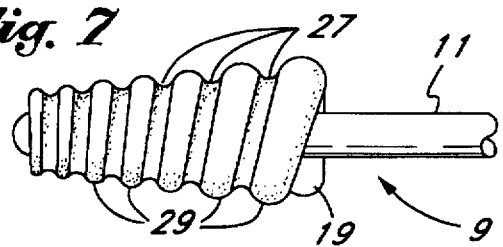

5,715,559

1

CLEANING TOOL

FIELD OF THE INVENTION

The present invention relates to the field of fiber based cleaning tools and more particularly to a stick support having a twisted fiber on at least one of the ends and twisted in the shape of a screw or circular inclined plane.

BACKGROUND OF THE INVENTION

Cleaning tools, especially disposable cleaning tools have been known for some time. One of the most popular is sold under the "Q-TIP" brand name and is a loose swab wrapped onto the end of a stick along a path perpendicular to the extent of the support stick. It is often referred to as a swab since the applied material, usually cotton, is positioned to readily unroll or slide off the end of the stick into a clumped mess once a liquid is encountered or once any significant axial forces are encountered.

The use of the swab for cleaning tape heads and the like is well known, even though the material loses its resiliency after a few rubs and typically falls off of the stick becoming a small mop. When the material falls off of the stick, a small portion of the inner material which still may be stuck to the stick is practically unavailable to absorb moisture. Thus, even as a mop, the device is ineffective to rein in materials and moisture since the working portion of the material is separated from and remote to the remaining portion of the material near the stick.

SUMMARY OF THE INVENTION

The cleaning tool of the present invention involves a stick or rod onto which the material or other absorbing media is wound in a spiral pattern to accomplish several results. First, since it is twisted, it will be unlikely to be removed from its place on the stick absent severe cleaning pressures or an abrasive surface. The material is rope-twisted as it is sprially wound on to the stick.

Secondly, since it is applied in a spiral or screw pattern, it will be a more effective cleaning tool since any of the debris being cleaned can collect in the grooves between the outer ridges of the rope twisted material to insure that the outer ridges of the spiral are always available for cleaning contact with the surface area to be cleaned and does not "mush" the material to be cleaned about the surface from which the material is to be cleaned.

In effect, the invention sets up at least two stages of absorptive/adsorptive cleaning. The outer fibers scrape the surface to be cleaned and begin to capture the material to be cleaned into the fibers. Where a large amount of material is present, the cleaning action will move this material into the spaces between the grooves of the spiral to give the contacting portions of the spiral more capacity to absorb/adsorb more material to be cleaned.

A first embodiment includes a rope twisted spiral of material applied directly to a stick. In a second embodiment, the rope twisted spiral is applied over a wound layer of material wound in the standard manner and at right angles to the axis of the stick. This embodiment is in effect a padded spiral with the rope twisted material being padded underneath and cushioned by the standard material winding.

In a third embodiment, a tightly spaced length of rope-wound material is attached to a stick. In a fourth embodiment, the tightly spaced length of rope-wound material is spiral cut to provide custom shaping to the ridges of the spiral shape.

2

In a fifth embodiment, an extruded length of material with a 30° angle is wrapped onto the rod to form sharply angled interstitial areas between adjacent portions of the extruded material. In a sixth embodiment, the cleaning surface and the rod are integrally formed as by injection molding or the like. In a seventh embodiment, a length of cut sponge is applied to the rod in a manner similar as that for application of the extruded length of material in the fifth embodiment. In an eighth embodiment, a conically shaped under layer of wound cotton supports an over layer of rope cotton having constant cross section. In a ninth embodiment, an integrated structure has an overall sharply tapered shape but with a constant angled spiral ridge outer surface.

BRIEF DESCRIPTION OF THE DRAWINGS

The invention, its configuration, construction, and operation will be best further described in the following detailed description, taken in conjunction with the accompanying drawings in which:

FIG. 1 is a plan view of a double ended cleaning tool having a rope twisted length of material applied in a relatively widely spaced fashion to the ends of the stick;

FIG. 2 is a closeup taken through line 2—2 of FIG. 1;

FIG. 3 is a cross section taken along the axis of the end of the cleaning tool shown in FIG. 2;

FIG. 4 is a cross sectional view of a second embodiment having the rope two layers including a conventionally applied lower layer and a twisted rope spiral applied outer layer;

FIG. 5 is a third embodiment of a tightly wound twisted rope spiral of material;

FIG. 6 is a cross section of the embodiment of FIG. 5;

FIG. 7 is a fourth embodiment wherein a spiral cut is introduced onto the spiral wound embodiment in FIG. 5 to deepen and widen the grooves;

FIG. 11 is a sixth embodiment wherein the stick or rod and the raised cleaning surfaces are integrally formed, as by injection molding and the like;

DETAILED DESCRIPTION OF THE PREFERRED EMBODIMENT

Figure 8:
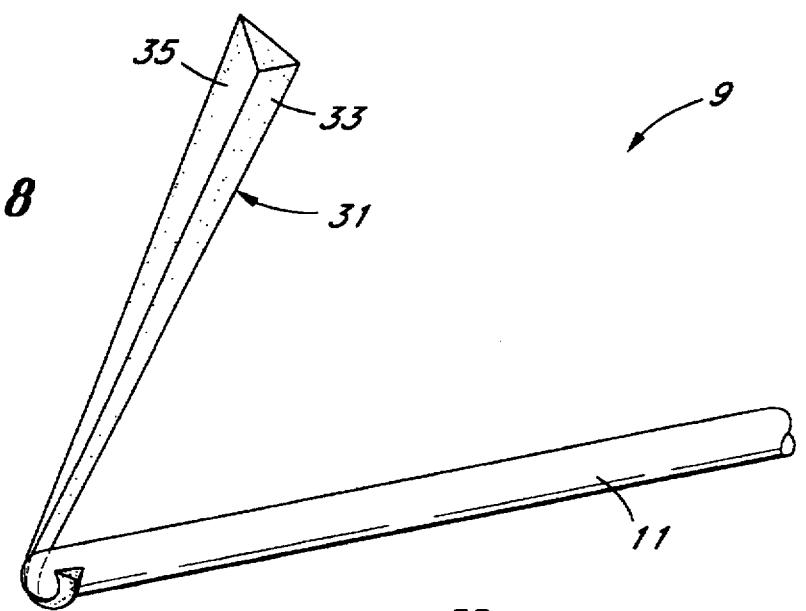
FIG. 8 is a fifth embodiment where a tapering length of extruded material is wound onto the end of a stick and illustrating one end of the cleaning device.

The description and operation of the invention will be best described with reference to FIG. 1. A first embodiment of a cleaning device 9 includes a rod 11 which may be made of wood, paper composite or plastic, and has a first end 13 and a second end 15. The rod 11 may be solid or hollow. First and second ends 13 and 15 are wound with a length of rope twisted material 17. The material 17 is ideally fibrous material which will exhibit material strength enhancement when rope twisted. The preferred material for the length of rope twisted material 17 is cotton fiber, although different types of fiber may be used depending upon the application to which the cleaning device 9 may put to use. Ideally, the length of rope twisted material has a relatively larger cross section at a first end 19 and tapers to a relatively smaller cross section at a second end 21. Also, for good absorptivity and adsorptivity, the preferred material for the length of rope twisted material 17 is cotton fiber.

By the term rope twist is meant any twisting along the longitudinal axis of the length of material 17 which is being laid down, and to distinguish this geometry from the twisting or wrapping of a wad of material onto a stick in the conventional way. The conventional way involves the wrapping of individual fibers about the end of the rod 11 within a plane perpendicular to the axis of the stick. By twisting the length of material along its axis before or at the time it is applied to the rod 11, it will have enhanced strength. It is clear that where the fibers are simply twisted along the axis of their length between their first end 19 and second end 21 that strength will be added to the resulting structure. Other variations on the twist, including braiding, twisting about multiple independent axes along the main axis of the twist, and the like will similarly cause strengthening.

In extreme cases, a very tight twist laid down in a tight manner can provide a cleaning tool able to withstand vigorous scrubbing action. Conversely where the twist is not as forceful and more gentle, a fluffier but weaker structure is formed. Depending upon the extent of tightness of the twist and the degree of taughtness with which the rope twisted material is wrapped around the rod 11, the resulting cleaning device 9 will be either stronger or weaker.

The details of the braiding will not be shown, nor will the central axis of the twist, since it can be symmetrical or asymmetrical with respect to the length of the rope twisted material 17.

As can be seen in FIG. 1, a relatively wide spacing is left between adjacent areas of the rope twisted material 17, actually exposing portions of the rod 11 in a set of interstitial spaces 23 so formed. This interstitial space accommodates any excess material to be removed while still allowing the outer surfaces of the rope twisted material 17 to continue to contact and clean the surface to which the cleaning tool 9 is applied.

The rope twisted material 17 may be affixed to the stick with any glue, adhesive or the like. Since the rope twisted material 17 has more integrity than simple wrapped material fibers, a stronger adhesive can be used to hold the whole structure of the rope twisted material 17 onto the end of the rod 11. Also the interstitial areas 23 are more clearly seen in FIG. 2.

Referring to FIG. 3, a sectional view of cleaning tool 9 of FIG. 2 is taken with respect to the rope twisted material 17, but not with respect to the rod 11. As can be seen, the rope twisted material 17 is preferably a single length of material, although it could be applied as a series of ring twists. In any such ring twist embodiment, the benefits of the spiral or screw shape would be lost.

Referring to FIG. 4, a second embodiment of the cleaning device 9 includes a conventionally wrapped under layer 25 which supports and cushions the overlying rope twisted material 17. In the case where the under layer 25 is not tapered, the rope twisted material 17 may be more sharply tapered. As can be seen, the general shape of the under layer 25 is the same as would be found with conventionally available swabs, in order to show that the invention of the second embodiment could begin with a conventionally wrapped swab and then have the rope twisted material 17 applied.

This is possible despite the fact that the thickness of the under layer 25 is almost inverse of a thickness desired for the overall shape of the spiral. In addition, the adhesive used for the rope twisted material 17 can also help by forming a spiral stiffness which helps it to hold its own shape independent of its surface contact with the under layer 25. Also, FIG. 4 shows a relatively loosely wrapped structure, but the rope twisted material 17 could be more tightly wrapped to further compress the under layer 25.

Referring to FIG. 5, in a third embodiment of the cleaning device 9, a tightly wrapped spiral of rope twisted material 17 is applied to the end of a rod 11. In this, there is not interstitial space 23 and the only spaced between the adjacent widths of rope twisted material 17 are at the points of their touching tangency.

Referring to FIG. 6, a sectional view of the tightly wound embodiment of FIG. 5 is shown. Although the adjacent widths of rope twisted material 17 show touching tangency, it is clear that as the tightness of the spiral structure increases, the individual cross sections may deviate from circularity to make deeper spaces between the lengths of rope twisted material 17. Conversely, a tighter rope twist for the rope twisted material 17 will resist lateral deformation and thus the tendency of the individual cross sections to deviate from circularity.

Referring to FIG. 7, a fourth embodiment of the cleaning device 9 illustrates a structure which enables more controlled spacing between adjacent sections of the lengths of rope twisted material 17. This is accomplished by circularly shaving or cutting sections of the lengths of rope twisted material 17 at the points of their adjacent contact. The cut groove lies along, and where cut, is cut along the spiral line of abutment of the lengths of rope twisted material 17. Since the lengths of rope twisted material 17 are spiral wound, they should also be spiral cut in order to keep from cutting the lengths of fiber short and thus diminishing the integrity of the fiber extension.

As an example, it is clear that the structure of FIG. 7 could not be effectively produced by taking an ordinary swab and cutting it in a spiral fashion, since the spiral cut would cut in a direction which is not wholly in line with the extent of the fibers of the lengths of rope twisted material 17. In such a case the average effective length of the fibers would be severely shortened causing the structural integrity to diminish and the shortened fibers to fall from the structure as lint.

It would be convenient from a manufacturing standpoint to perform the cutting operation as the lengths of rope twisted material 17 were being added to the rod 11. In the alternative, the lengths of rope twisted material 17 could be pre-formed such that when wrapped on the stick they assume the shape of FIG. 7. Pre-forming or pre-shaping enables the use of a tightly formed spiral, but with the ability to control the topography of the resulting structure. By cutting into the structure spirally, the overall integrity of each length of rope twisted material 17 is not compromised.

As can be seen in FIG. 7, the cut portion produces a series of relatively shallow troughs 27 which are bounded by the uncut outer surfaces 29. The depth and widths of the troughs 27 can be controlled by controlling the depth and width of the cut. The area of the outer surfaces 29 left exposed will depend upon and be inversely proportional to the width of the troughs 27 cut into the laterally compactly wound lengths of rope twisted material 17.

Referring to FIG. 8, an embodiment is shown in which an extruded material is wound on the stick 11. An extruded material 31 is formed in the shape of an elongate tapering material having a triangular cross shape. The taper is formed by raising the base to an ever narrowing base width while leaving the upper portion of the triangular shape at the same angle.

The extruded material 31 has a base surface 33 and a pair of side surfaces 35. Since the taper is in the upward direction normal with respect to with respect to the base surface 33, the base 33 of the tapering extruded material 31, is formed in a single plane, albeit a tapering one. Since the taper reduces the width of the base, there will be more winds per unit length of the stick at the smaller end. FIG. 8 illustrates that the extruded material 31 can be applied by winding it on the stick 11, here shown beginning with the narrow end of the tapering extend of the extruded material 31.

Referring to FIG. 8, the extruded material 31 has been wound onto and fixed upon the stick 11. The extruded material can be affixed by an adhesive applied either to the end of the stick 11, or to the base 33 of the extruded material 31. Further glue could be applied to the lowermost base surface 33 of the extruded material 31 and partially up along only the lowermost area of the side surfaces 35 to enable the side surfaces 35 to stick together.

Figure 9:
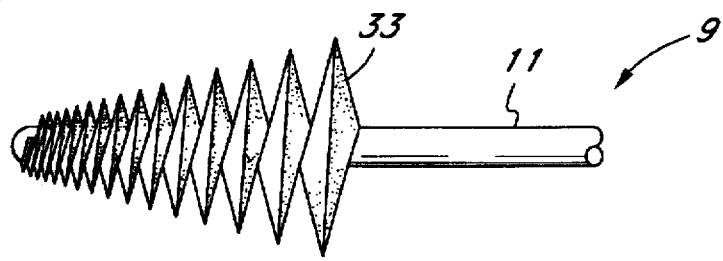
FIG. 9 is a view of an end of the completed cleaning device being formed in FIG. 8.
Figure 10:
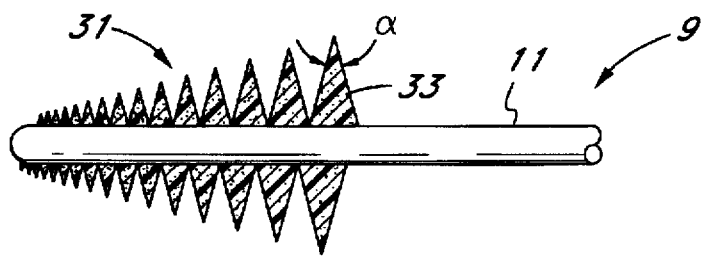
FIG. 10 is a partial sectional view of the cleaning device of FIGS. 9 & 10 and illustrating the positioning of the extruded material on the stick, and the angularity of the outermost apex of each section of extruded material.

Referring to FIG. 10, a semi sectional view of the embodiments of FIGS. 8 & 9 show the angle α which is the angle between the side surfaces 35 at the circumferential outside of the wound length of extruded material 31. The angle α is ideally a 30° angle, but the angle may be increased or decreased. The 30° angle creates significant spaces between each section of extruded material 31 in order to accommodate removed debris in the cleaning tool 9 and to facilitate removal of the debris as it clings to cleaning tool 9 between the adjacent sections of the wound length of extruded material 31.

Figure 11:
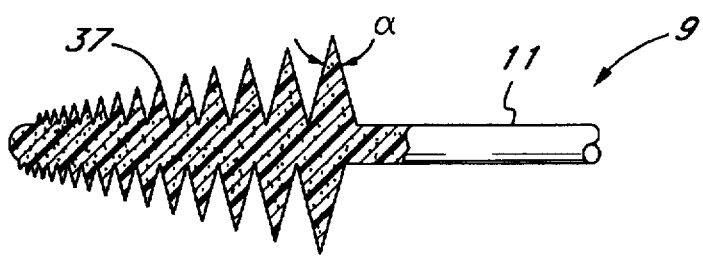

Referring to FIG. 11, a semi-sectional view of a fifth embodiment is shown wherein the rod 11 and a cleaning surface 37 are integrally formed. Ideally the formation of the end of cleaning device 9 of FIG. 11 is by injection molding or the like. Given that the color and softness of the materials can be widely substituted, it is clear that the cleaning tool 9 can be made which is soft enough to bend the rod 11 when it is being used. It could be made from any material. For example, where the rod 11 is of wood, the end of the cleaning tool 9 can be cuttably formed from a single piece of material. At the other end of the spectrum, the cleaning tool 9 of FIG. 11 can be formed from a foamed rubber or soft plastic.

Figure 12:
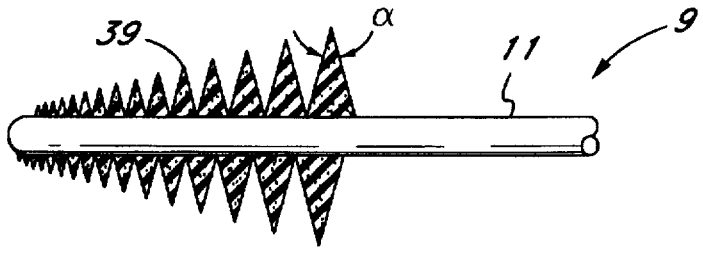
FIG. 12 illustrates a seventh embodiment wherein a cut sponge material is used to form the cleaning tool of the present invention.

Referring to FIG. 12, a sixth embodiment illustrates a cleaning tool 9 having an end of cut sponge 39 applied to a rod, in a manner similar to that of FIG. 8, or perhaps as a shape cut from a single block of sponge. The sponge 39 acts to clean as shown in the other Figures, but also has an enhanced capability to absorb liquids.

Figure 13:
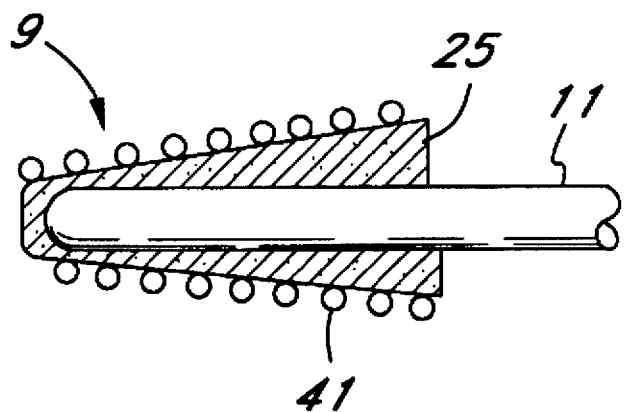
FIG. 13 illustrates a cross section of an eighth embodiment having a conically shaped under layer of wound cotton, and an over layer of rope cotton having constant cross section.

Referring to FIG. 13, a cross sectional view of an eighth embodiment illustrates a conventionally wrapped under layer 25 formed into a frusto conical shape and supporting an over wrapped layer of rope cotton 41 having constant cross section. This enables the bulk of the angularity to come from the under layer 25 and provides a uniform space between adjacent extents of rope cotton 41.

Figure 14:
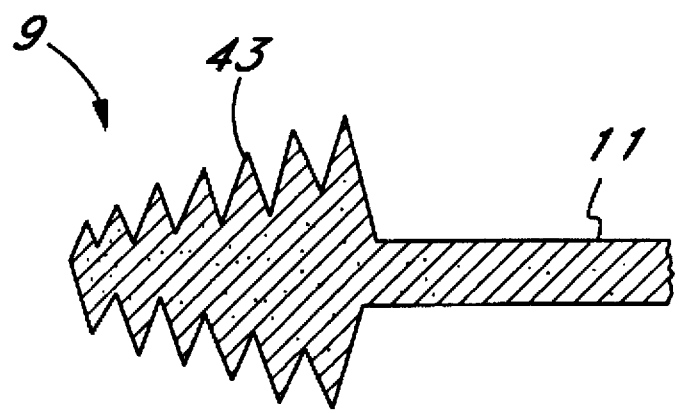
FIG. 14 is an integrally made ninth embodiment having an overall sharply taperted shape but with a constant angled spiral ridge outer surface.

Referring to FIG. 14, a ninth embodiment includes an integrally formed structure having constant angled ridges 43 which provide a more sharply angled overall shape. The taper is abrupt while maintaining a constant angled spiral ridge outer surface.

While the present invention has been described in terms of a cleaning tool as well as structures and methods for both forming and shaping the cleaning tool to enable a stronger, more absorptive/adsorptive cleaning tool and a disposable cleaning tool having greater utility, one skilled in the art will realize that the structure and techniques of the present invention can be applied to many similar devices. The present invention may be applied in any situation where strength and physical ability to remove debris is desired.

Although the invention has been derived with reference to particular illustrative embodiments thereof, many changes and modifications of the invention may become apparent to those skilled in the art without departing from the spirit and scope of the invention. Therefore, included within the patent warranted hereon are all such changes and modifications as may reasonably and properly be included within the scope of this contribution to the art.

What is claimed:

1. A cleaning tool comprising:
   an elongate rod having a first end and a second end;
   a length of rope twisted material wrapped about said elongate rod near said first end.

2. The cleaning tool of claim 1 wherein said length of rope twisted material is made of cotton.

3. The cleaning tool of claim 1 wherein said length of rope twisted material forms a tight spiral and where adjacent lengths of said rope twisted material abut each other.

4. The cleaning tool of claim 3 wherein a spiral, rounded groove is cut along the spiral line of abutment of said adjacent lengths of said rope twisted material.

5. The cleaning tool of claim 4 wherein said length of rope twisted material has a first end and a second end and said length of rope twisted material has a first diameter near said first end of said length of rope twisted material and a second diameter near said second end of said length of rope twisted material larger than said first diameter, measured irrespective of said spiral groove.

6. The cleaning tool of claim 5 wherein said first end of said length of rope twisted material lies nearer said first end of said rod than said second end of said length of rope twisted material.

7. The cleaning tool of claim 1 wherein said length of rope twisted material forms a spiral interstitial space between adjacent lengths of said rope twisted material.

8. The cleaning tool of claim 1 wherein said length of rope twisted material has a first end and a second end and said length of rope twisted material has a first diameter near said first end of said length of rope twisted material and a second diameter near said second end of said length of rope twisted material larger than said first diameter.

9. The cleaning tool of claim 8 wherein said first end of said length of rope twisted material lies nearer said first end of said rod than said second end of said length of rope twisted material.

10. The cleaning tool of claim 1 wherein said length of rope twisted material is a first length of rope twisted material and further comprising a second length of rope twisted material wrapped about said elongate rod near said second end.

11. The cleaning tool of claim 1 and further comprising an under layer of material wrapped around said rod at right angles to a main axis of said rod and wherein said length of rope twisted material is wrapped about said elongate rod over said under layer of material.

12. The cleaning tool of claim 11 wherein said length of rope twisted material forms a loose spiral wherein portions of said underlayer between adjacent lengths of said rope twisted material is externally exposed.

13. The cleaning tool of claim 11 wherein said length of rope twisted material has a first end and a second end and said length of rope twisted material has a first diameter near said first end of said length of rope twisted material and a second diameter near said second end of said length of rope twisted material larger than said first diameter.

14. The cleaning tool of claim 13 wherein said first end of said length of rope twisted material lies nearer said first end of said rod than said second end of said length of rope twisted material.

15. A cleaning tool comprising:

an elongate rod having a first end and a second end;

a length of material tapered in two dimensions spirally wrapped about said elongate rod near said first end.

16. The cleaning tool of claim 15 wherein said length of tapered material has a triangular cross sectional area.

17. The cleaning tool of claim 16 wherein said length of tapered material's triangular cross sectional area has a pair of equal length side surfaces and a base surface.

18. The cleaning tool of claim 16 wherein said length of tapered material has an circumferentially outermost edge having an angle of about 30°.

19. The cleaning tool of claim 15 wherein said length of tapered material is made of sponge.

20. The cleaning tool of claim 15 wherein said length of tapered material has a first end and a second end of greater cross sectional area than said first end of said length of said tapered material and said first end of said tapered material is located nearer said first end of said rod than said second end of said length of tapered material.

* * * * *